United States Patent [19]
Alonso

[11] Patent Number: 4,892,541
[45] Date of Patent: Jan. 9, 1990

[54] HEART VALVE PROSTHESIS

[75] Inventor: Manuel T. Alonso, Newport Beach, Calif.

[73] Assignee: Tascon Medical Technology Corporation, Minneapolis, Minn.

[21] Appl. No.: 8,207

[22] Filed: Jan. 29, 1987

Related U.S. Application Data

[60] Division of Ser. No. 664,150, Oct. 24, 1984, Pat. No. 4,680,031, which is a continuation-in-part of Ser. No. 445,259, Nov. 29, 1982, abandoned, which is a continuation-in-part of Ser. No. 303,345, Oct. 7, 1982, abandoned.

[51] Int. Cl.$^4$ ................................................ A61F 2/24
[52] U.S. Cl. ......................................... 623/2; 623/900
[58] Field of Search ...................... 623/900, 2; 72/199; 427/2, 193

[56] References Cited

U.S. PATENT DOCUMENTS

| | | | |
|---|---|---|---|
| 2,659,252 | 5/1952 | Kipp | 72/199 X |
| 3,714,671 | 2/1973 | Edwards et al. | 623/2 |
| 3,983,581 | 10/1976 | Angell et al. | 623/2 |
| 4,035,849 | 7/1977 | Angell et al. | 623/2 |
| 4,044,170 | 8/1977 | Scharbach et al. | 427/193 X |
| 4,106,129 | 8/1978 | Carpentier et al. | 623/2 |
| 4,388,735 | 6/1983 | Ionescu et al. | 623/900 X |
| 4,441,216 | 4/1984 | Ionescu et al. | 623/900 X |
| 4,626,255 | 12/1986 | Reichart et al. | 623/900 X |

Primary Examiner—Alan W. Cannon
Attorney, Agent, or Firm—Reed A. Duthler; Joseph F. Breimayer

[57] ABSTRACT

A "tissue valve type" heart valve prosthesis is disclosed which has a biocompatible plastic sewing ring adapted to be surgically implanted into the mitral, aortic or tricuspid annulus of the human heart. The sewing ring has internal square threads and a biocompatible fabric mesh or cloth is embedded into the sewing ring so that the cloth can be fully wrapped around the sewing ring covering all of its plastic surfaces except for the internally protruding threads. A biocompatible plastic stent support ring has externally disposed threads to lock with the threads of the sewing ring in approximately one turn, or less. The stent support ring also embeds a biocompatible fabric mesh which can be wrapped around the stent support ring to cover all of its plastic surfaces, except for the protruding threads, and to form a cloth pocket wherein a solid stent is mounted. A porcine trileaflet valve is mounted to the stent. When the heart valve prosthesis is as implanted into the heart, the threads of the sewing ring and of the stent support ring interlock, and there are no plastic or metal surfaces, uncovered by biocompatile fabric, to be exposed to blood flow. Processes for making the solid metal stent by laser cutting, and the sewing and stent support rings by a specifically adapted plastic molding procedure, are also disclosed.

6 Claims, 4 Drawing Sheets

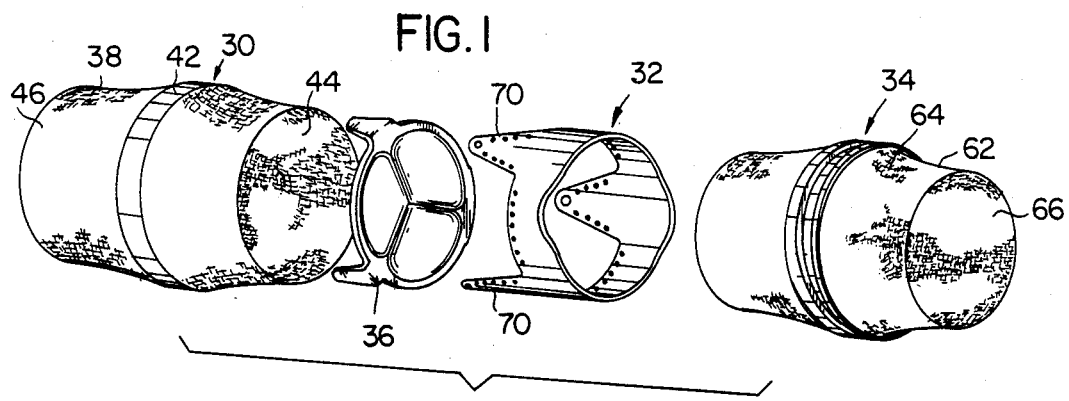
FIG. 1
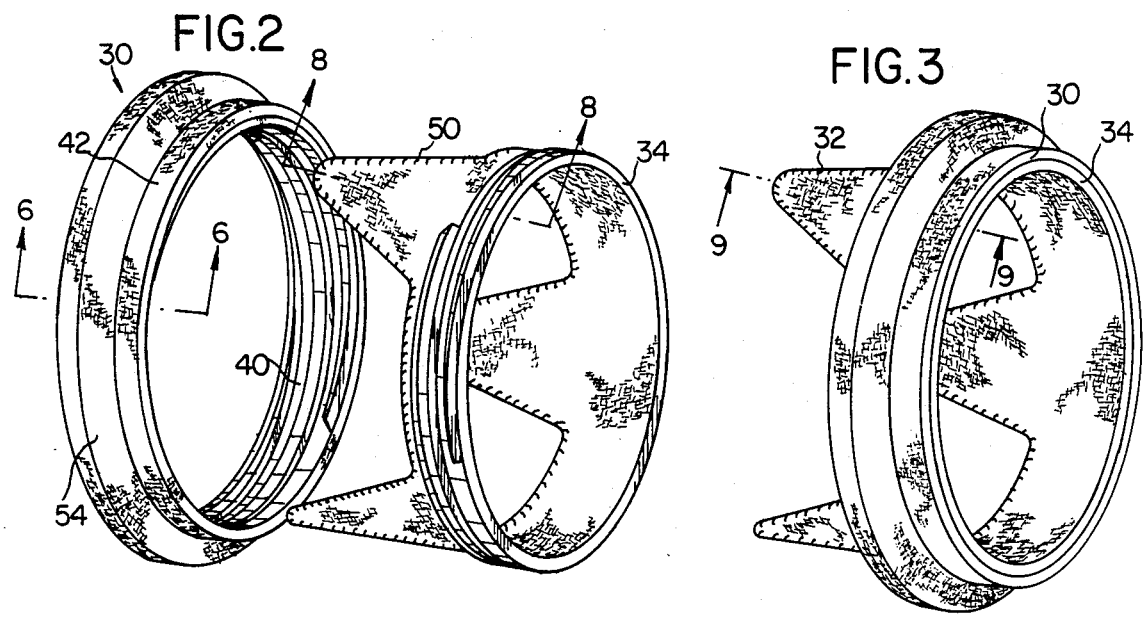
FIG. 2
FIG. 3
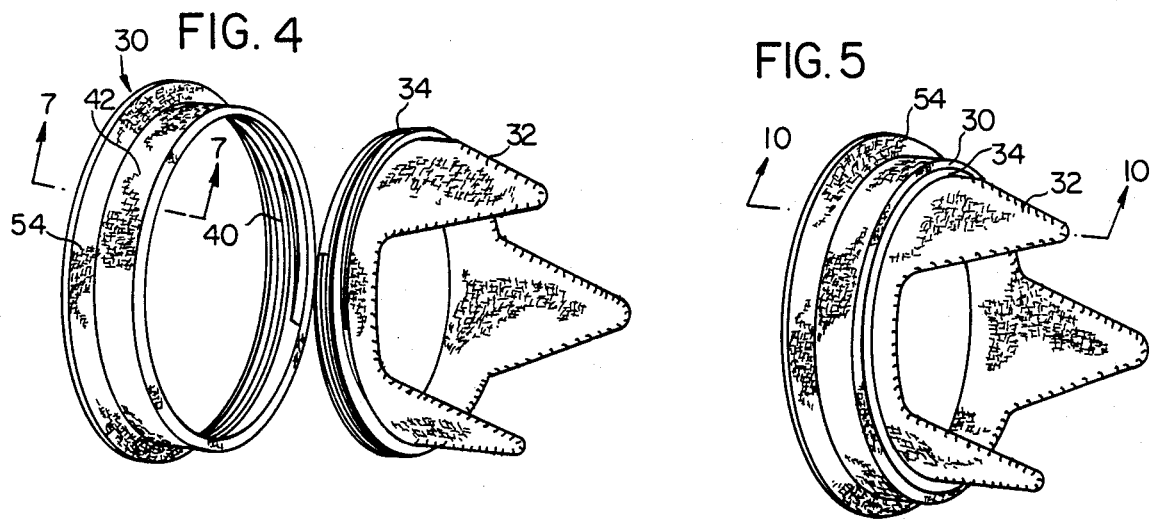
FIG. 4
FIG. 5

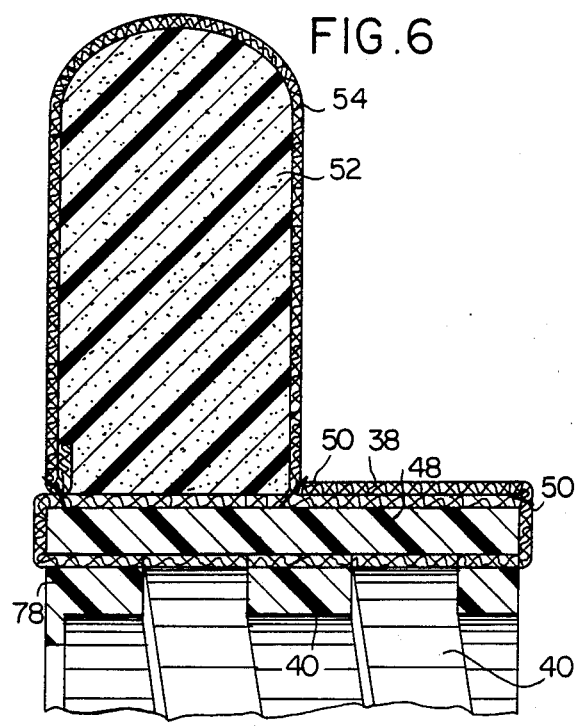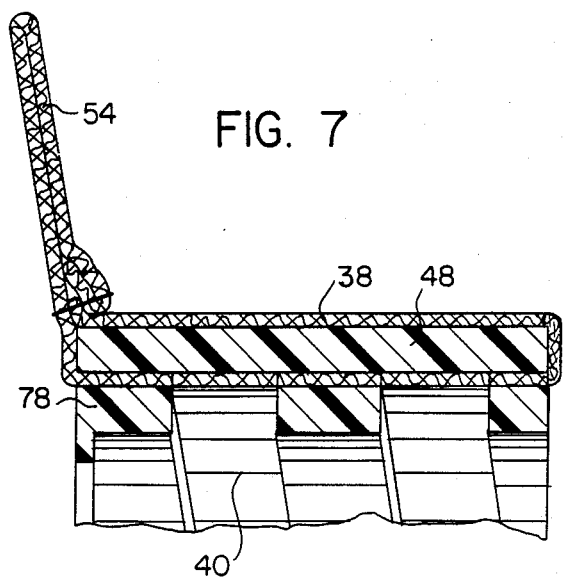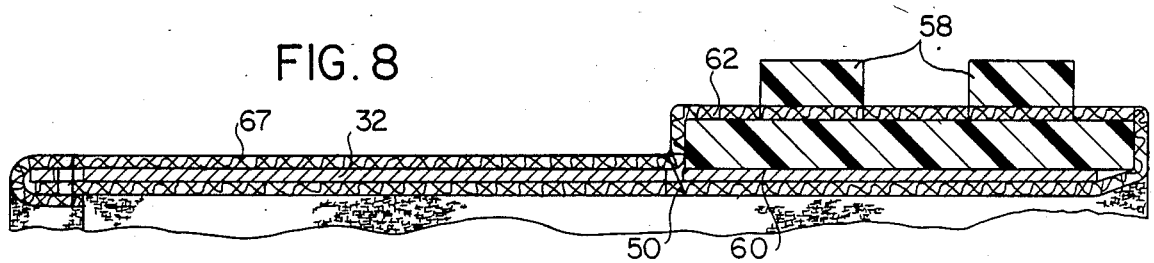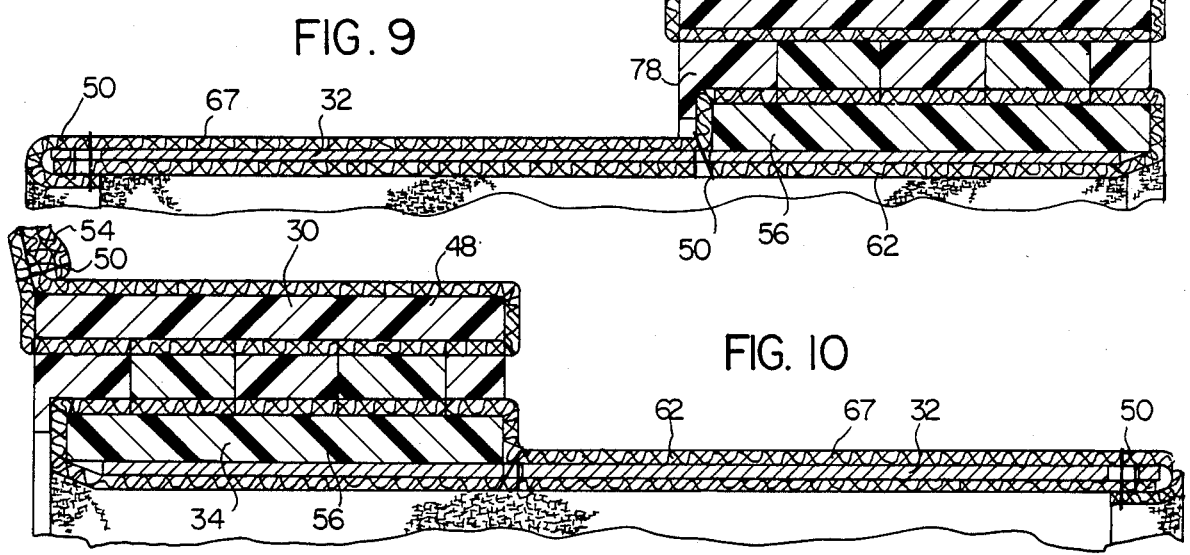

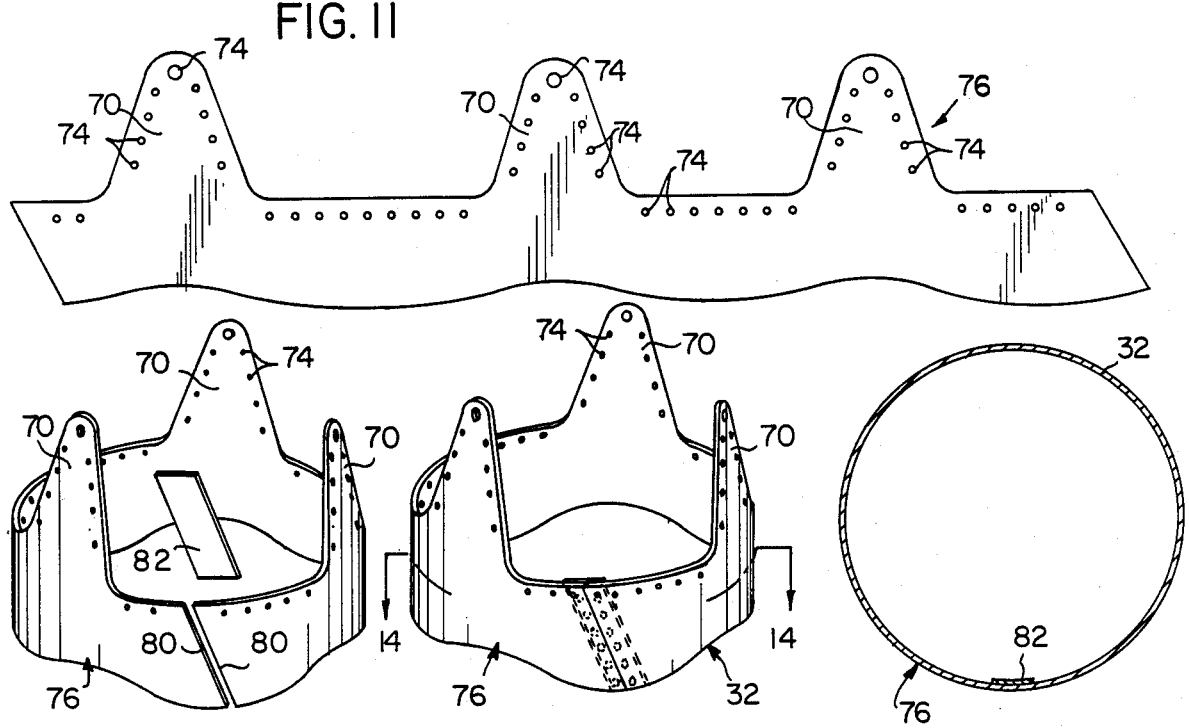
FIG. 11
FIG. 12
FIG. 13
FIG. 14
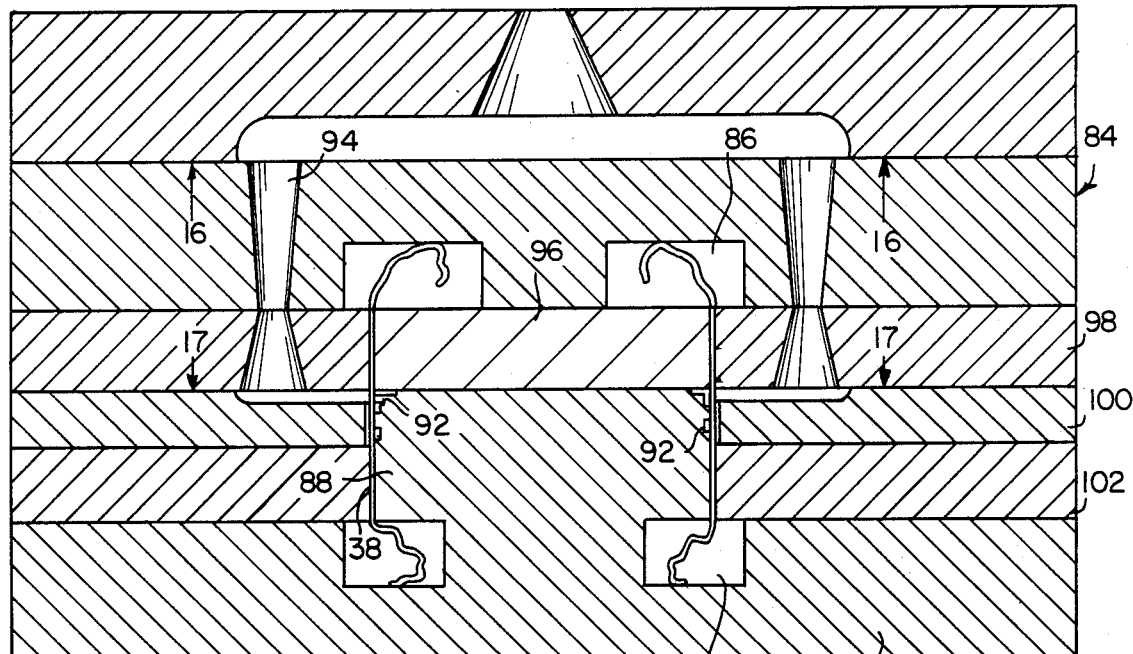
FIG. 15

HEART VALVE PROSTHESIS

This is a divisional of co-pending application Ser. No. 664,150, filed on Oct. 24, 1984 which is now U.S. Pat. No. 4,680,031, which is a continuation-in-part of Ser. No. 445,259, filed on Nov. 29, 1982, now abandoned, which is a continuation-in-part of Ser. No. 303,345, filed on Oct. 7, 1982, now abandoned.

BACKGROUND OF THE INVENTION

1. Field of the Invention

The present invention is in the field of heart valve implantations. More particularly, the present invention is directed to artficial heart valves of the type which include a sewing ring to be permanently installed in the heart, and a tissue valve mounted to a stent removably attachable to the sewing ring.

2. Brief Description of the Prior Art

Two major types of heart valve implantations are known in the prior art. One of these, includes a metal or plastic artificial valve structure which regulates the direction of the blood flow in the anatomical structure wherein the heart valve is incorporated. By their very nature, these "mechanical type" heart valves have metal or plastic surfaces exposed to the blood flow, which remain thrombogenic even long time after their implantation by major surgery. Therefore, patients wearing such "mechanical type" heart valves can avoid potentially life threatening embolus formation only by constantly taking anti-thrombogenic medication, such as cumadine.

Another major type of artificial heart valve implant utilizes a tissue valve of animal (principally porcine) origin to regulate the direction of blood flow. Such porcine "tissue valves" include three cusps or leaves of a heart valve excised from pigs and preserved by treatment with glutaraldehyde. The animal tissue portion of the artificial "tissue valves" is, generally speaking, not thrombogenic. Therefore, at least some time after the surgical implantation of the artificial "tissue valves", the human patient would not necessarily require anti-thrombogenic medication (cumadine), unless, of course, some other portion of the artificial valve implantation includes thrombogenic metal or plastic surfaces exposed to the blood flow. Therefore, designers of the tissue valve type heart valve implants have, generally speaking, strived to minimize the plastic and metal surfaces of artificial heart valves which are exposed to blood flow.

Another important goal of artifical heart valve design is to minimize obstruction of blood flow in the anatomical structure wherein the artificial valve is implanted, i.e. to maximize the unobstructed flow passage area in the mitral, aortic or tricuspid annulus wherein the artificial valve is surgically mounted.

Still another goal is to render the "working" (flow direction regulating) valve structure replaceable without the need for surgically removing and destroying heart tissue in the annulus where the valve implant is mounted by sutures.

In efforts to attain the above-noted and related goals, the prior art has provided artificial heart valve implants which include a sewing ring and a valve structure removably mountable to the sewing ring. The sewing ring is, usually, a short section of a tube which is attached to a suitable biocompatible cloth or fabric. The sewing ring is surgically sewn (sutured) to the heart tissue.

The remainder of the artificial heart valve implant, whether it is the "mechanical" or "tissue valve" type, usually includes a support structure for the valve mechanism, with the support structure being securable by some type of locking mechanism to the sewing ring. The locking mechanism include threads in the sewing ring and complementary threads in the support structure. In addition to the foregoing, the prior art has also provided heart valve implants of the type wherein the sewing ring is integral (i.e. not removable during surgery), with the rest of the valve structure.

The valve support structure of the removable (and also non removable) tissue valve type heart valve implants usually includes a stent. The stents of the prior art usually comprise a bent wire structure made of a biocompatible, non-corrosive metal, such as stainless steel, or preferably a cobalt - nickel alloy known under the ELGILOY trade name. The stent typically includes a circular base and three stent posts (commissural posts) configured in such a manner that the three cusps of the porcine tissue heart valve can be attached to and are operatively supported by the commissural posts. In some prior art artificial valve implants, the stent is covered by a porous biocompatible fabric or cloth into which human tissue in-growth can occur after implantation, so as to reduce the risk of potentially dangerous blood clot formation.

Specific examples of prior art artifical heart valve implants are found in U.S. Pat. Nos. 3,744,062; 3,835,475; 3,997,923; 4,364,126 and 4,106,129. U.S. Pat. Nos. 4,211,325; 4,319,363 and 4,257,444 disclose subject matter which is of general background interest to the present invention.

The above-summarized prior art heart valves, including those disclosed in the above-cited patents, generally speaking, suffer from the following disadvantages. Plastic or metal surfaces of the valve implants remain exposed to the blood flow even in the "tissue valves" of the prior art, so that the patient wearing the valve implant must depend on anti-thrombogenic medication in order to avoid potentially lethal blood clot formation.

The configuration of the wire stent is often less than optimal for the mounting and prolonged functioning of the trileaflet (three-cusp) porcine valve. In addition, bent wire made of stainless steel, and particularly of cobalt - nickel alloy (ELGILOY), is not ideally suited for forming the stent from a structural integrity standpoint, even though ELGILOY is quite satisfactory from the standpoint of corrosion resistsance and biocompatibility. This is because, in order to provide adequate strength the wire must be fairly thick, and the thickness of the wire substantially reduces the flow-through area in the annulus wherein the valve implant is mounted. Moreover, in order to provide the necessary commissural posts in the stent, the wire of the stent must be subjected to relatively sharp bends which adversely affect its structural integrity. In this regard it is noted that for the making of certain stents for tissue valves, ELGILOY wire must be bent to a greater extent than what is considered acceptable by the manufacturers of the wire.

Still further, in the prior art heart valve prostheses which have a bent wire stent, an additional plastic support member must be mounted in the stent to operatively support the trileaflet porcine tissue valve. The need for this additional support member, of course, complicates the assembly of the heart valve prosthesis, and increases its cost.

Finally, the process of mounting the stent bearing the tissue valve, (or mechanical valve) to the sewing ring is difficult because of the conditions prevailing during open heart surgery, regardless of the structure of the valve implant. The prior art valve implants which had relatively complex mounting mechanisms have, generally speaking, rendered the task of the surgeon more difficult than desirable and exposed the patient to high risk.

In light of the foregoing, there is a genuine need in the prior art for improved artifical heart valve designs which overcome the above-noted disadvantages. The present invention provides such artificial heart valve designs.

SUMMARY OF THE INVENTION

It is an object of the present invention to provide an artificial heart valve implant of the "tissue valve" type which contains virtually no metal or plastic surfaces exposed to the blood flow, whereby the patient wearing the implant does not require continuous anti-thrombogenic medication.

It is another object of the present invention to provide an artifical heart valve implant which is designed to maximize the area available for blood flow in the mitral, aortic or tricuspid annulus where the implant is surgically mounted.

It is still another object of the present invention to provide an artificial heart valve implant wherein the stent supporting the valve structure is not subjected to undue bending stresses which adversely affect its structural integrity.

It is yet another object of the present invention to provide an artificial heart valve implant of the type having a sewing ring permanently attachable to the human heart, and a valve structure removably attachable to the sewing ring, wherein mounting and de-mounting of the valve structure to the sewing ring can be readily performed under the conditions of open heart surgery.

The foregoing and other objects and advantages are attained by an artificial heart valve implant which has a sewing ring having interior threads, and a stent support ring having exterior threads so that the stent support ring is threadably mountable into the sewing ring. The sewing ring and the stent support ring are made of biocompatible thermoplastic material. Preferably, the threads are square threads of the type which lock the sewing ring and the stent support ring to one another in less than one turn.

A first cloth of a biocompatible fabric mesh is embedded in the sewing ring so that the internal threads of the sewing ring and the exterior wall of the sewing ring are disposed on different sides of the first cloth. The first cloth is folded over the external wall of the sewing ring to form a cloth ring which is adapted to be secured by sutures into the mitral, aortic or tricuspid annulus in the human heart.

A second cloth of biocompatible fabric mesh is embedded in the stent support ring in an analogous manner, and the second cloth is folded over the internal, non-threaded wall of the stent support ring to provide a cloth pocket into which a metal stent of the heart valve prosthesis is mounted to fully enclose the stent in the cloth. Preferably, in accordance with the present invention, the stent is a substantially solid tubular metal member, which has a plurality of apertures to permit affixation of the cloth to the stent.

The sewing ring and the stent support ring are manufactured integrally with the respective cloth of fabric in a plastic molding process. This process comprises a separate aspect of the present invention. In the process, the cloth is first placed in a mold and molten plastic is injected under high pressure to flow through a portion of the cloth and to form the sewing ring and stent support ring, respectively, integral with the cloth.

The features of the present invention together with further objects and advantages, can be best understood from the following description, taken together wih the appended drawings, wherein like numerals indicate like parts.

BRIEF DESCRIPTION OF THE DRAWINGS

FIG. 1 is a perspective view showing the four major components of the heart valve prosthesis of the present invention, before the components are assembled to one another;

FIG. 2 is a perspective view showing a cloth covered sewing ring, stent and stent support ring of a mitral heart valve prosthesis in accordance with the present invention;

FIG. 3 is a perspective view of the components shown on FIG. 2, said components having been assembled to one another;

FIG. 4 is a perspective view showing a cloth covered sewing ring, stent and stent support ring of an aortic heart valve prosthesis in accordance with the present invention;

FIG. 5 is a perspective view of the components shown on FIG. 4, said components having been assembled to one another;

FIG. 6 is a cross-sectional view taken on lines 6,6 of FIG. 2;

FIG. 7 is a cross-sectional view taken on lines 7,7 of FIG. 4;

FIG. 8 is a cross-sectional view taken on lines 8,8 of FIG. 2;

FIG. 9 is a cross-sectional view taken on lines 9,9 of FIG. 3;

FIG. 10 is a cross-sectional view taken on lines 10,10 of FIG. 5;

FIG. 11 is a top view of a flat plate intermediate used in the fabrication of a preferred embodiment of the stent of the present invention;

FIG. 12 is a perspective view of another intermediate in the process of fabricating the stent of the present invention;

FIG. 13 is a perspective view of the preferred embodiment of the stent of the present invention;

FIG. 14 is a cross-sectional view of the stent shown on FIG. 13, the view being taken on lines 14,14 of FIG. 13;

FIG. 15 is a cross-sectional view of a mold used in the process of fabricating the novel sewing ring of the present invention;

DESCRIPTION OF THE PREFERRED EMBODIMENTS

Figure 16:
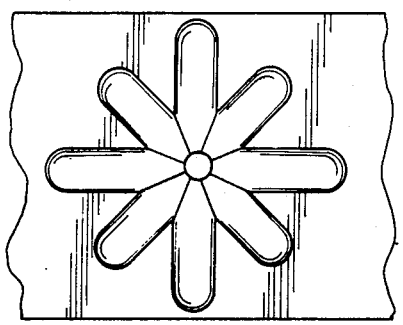
FIG. 16 is a partial plan view taken on lines 16,16 of FIG. 15.
Figure 17:
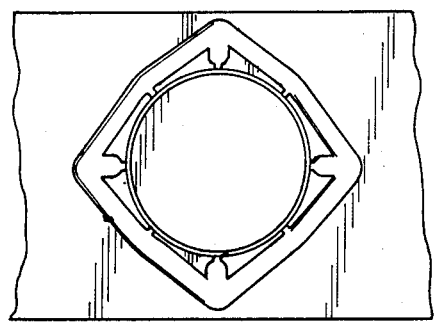
FIG. 17 is a partial plan view taken on lines 17,17 of FIG. 15.

The following specification taken in conjunction with the drawings sets forth the preferred embodiment of the present invention. The embodiment of the invention disclosed herein is the best mode contemplated by the inventor for carrying out his invention in a commercial environment, although it should be understood that various modifications can be accomplished within the parameters of the present invention.

Referring now to the drawing Figures, the preferred embodiments of the heart valve prostheses of the present invention are disclosed. It should be noted at the outset in this regard that mitral, aortic and tricuspid heart valve prostheses of various sizes can be fabricated by applying the generic principles and teachings of the present invention which are disclosed below. Moreover, the glutaraldehyde preserved porcine tissue valves which are incorporated in the heart valve prostheses of the present invention for regulating the direction of blood flow in the prostheses, are well known in the art. Therefore, for the sake of lucidity of the appended drawings, the porcine tissue valve is shown only schematically and only on FIG. 1. It should also be remembered that certain generic principles of the invention disclosed herein are also applicable for the construction of mechanical type heart valves, and even for the construction of other types of implantation devices.

Referring now to FIG. 1, the four major components of the heart valve prostheses of the present invention are shown before the components are assembled to one another. The four components are: a sewing ring 30, a stent 32, a stent support ring 34 and the porcine tissue valve 36. Among these components, the porcine tissue valve 36 is standard (as noted above), and is described in the present specification only to the extent necessary to disclose its relationship to the other novel components.

The novel sewing ring 30, and stent support ring 34 of the heart valve prostheses of the present invention are best explained with reference to FIGS. 2 through 10. Among these, FIGS. 2, 3, 6, 8 and 9 illustrate a mitral heart valve prosthesis (without showing the porcine tissue valve 36), and FIGS. 4, 5 7 and 10 illustrate an aortic heart valve prosthesis (also without showing the porcine tissue valve 36).

The sewing ring 30 is a relatively short tube section made of a biocompatible thermoplastic material, such as polypropylene, polyacetate or polycarbonate. It includes a first cloth tube 38, square threads 40 in its interior, and a smooth exterior wall 42.

A principal novel feature of the sewing ring 30 is that it embeds the first cloth tube 38 in the manner illustrated in the drawing Figures, so that the interior threads 40 of the sewing ring 30 are disposed within the interior 44 of the first cloth tube 38 and the exterior wall 42 of the sewing ring 30 is disposed on the exterior 46 of the first cloth tube 38. Thus, the first cloth tube 38 is integrally constructed with the plastic body 48 of the sewing ring 30.

For the fabrication of a sewing ring 30 for a mitral heart valve prosthesis, the first cloth tube 38 is folded over the external wall 42 of the sewing ring 30 to fully enclose the plastic body 48 of the sewing ring 30, except for the internally protruding threads 40. As is best shown on the cross-sectional views of FIGS. 6 and 9, the first cloth tube 38 is also folded over itself and is secured with stitches 50 to capture a suitable elastic member 52, which is made of a biologically compatible rubber or like material. This structure provides a padded cloth ring 54 which is substantially concentrical with the plastic body 48 of the sewing ring 30. In this regard it is noted that FIG. 1 illustrates the sewing ring 30 as an intermediate, having the embedded first cloth tube 38, before the cloth tube 38 is folded, trimmed and stitched to capture the elastic member 52.

For the fabrication of a sewing ring 30 for an aortic heart valve prosthesis in accordance with present invention, essentially the same steps of folding the first cloth tube 38, and trimming and stitching the same are followed. For essentially anatomical reasons, which are well understood by those skilled in the art, the cloth ring 54 of an aortic heart valve prosthesis, however, does not incorporate an elastic member. The structure, of the sewing ring 30 of an aortic heart valve prosthesis of the present invention is best shown on the cross-sectional views of FIGS. 7 and 10.

The stent support ring 34 of the heart valve prostheses of the present invention is best shown on FIGS. 8, 9 10. Thus the stent support ring 34 also includes a plastic body 56 which has exterior square threads 58, and an interior wall 60. A second cloth tube 62 is embedded in the plastic body 56 of the stent support ring 34 in such a manner that the exterior threads 58 of the stent support ring 34 are disposed on the exterior 64 of the second cloth tube 62, and the interior wall 60 of the stent support ring 34 is disposed within the interior 66 of the second cloth tube 62. The dimensions and configuration of the stent support ring 34 is selected in such a manner that the stent support ring 34 is threadably mountable to the sewing ring 30, as is shown on FIGS. 3, 5, 9 and 10.

In order to assemble the stent 32 to the stent support ring 34 for the heart valve prostheses fabricated in accordance with the present invention, the second cloth tube 62 is folded over the interior wall 60 of the stent support ring 34. In this manner, the stent support ring 34 is fully enclosed in the second cloth tube 62 and a cloth pocket 67 is formed wherein the stent 32 is mounted by sewing and stitches 50.

It should be apparent from the foregoing description and from inspection of the drawing Figures, that the first cloth tube 38 and the second cloth tube 62 are embedded in the threads 40 and 58 of the respective rings 30 and 34, in the sense that the cloth tubes form the valleys of the threads. This is an important advantage over prior art sewing rings and stent support rings because the embedded cloth is more securely attached to the rings than if the cloth were attached merely by adhesives (not shown), rivets (not shown) or like mechanical fasteners. In addition, in some prior art heart valve prosthesis cloth is placed over the threads before fastening. This is clearly not necessary in the heart valve prosthesis of the present invention.

Moreover, it should be apparent from the foregoing, that the stent support ring 34 bearing the untrimmed second cloth tube 62, as is illustrated in FIG. 1, is merely an intermediate in the fabrication of the final form of the stent support ring 34 which is incorporated in the heart valve prostheses of the present invention.

The first and second cloth tubes 38 and 62 embedded in the sewing and stent support rings 30 and 34 of the heart valve prostheses of the present invention, comprise a fabric mesh of a biocompatible plastic material, preferably polyester (polyacetate) fabric. The use of such fabric mesh to enclose various plastic and metal members which are subsequently surgically implanted in the human body, is, per se, known in the art. As is well known, after implantation into the human body, an ingrowth of collageneous tissue usually forms in the interstitial spaces of the fabric, and endothelial cells cover the fabric to provide a non-thrombogenic autologous surface. Therefore, at least sometime after the implantation, the cloth covered plastic or metal members no longer cause coagulation of blood, and present no significant danger of embolus formation when implanted in the heart. The fabric mesh or cloth of the first and second cloth tubes, as similar fabric used in the art, is relatively thin, preferably it is approximately 0.3 mm thick.

Referring now principally to FIGS. 1, and 13, the stent 32 incorporated in the heart valve prostheses of the present invention is described. The stent 32 of the present invention is a substantially tubular member formed from a substantially solid, thin plate 68 of a biocompatible metal, such as stainless steel or a cobalt - nickel alloy. Preferably, the stent 32 is formed from a substantially solid plate 68 of the proprietary cobalt-nickel alloy known under the ELGILOY trade mark.

The stent 32 incorporates three commissural posts 70 which are configured for optimal support of the three cusps 72 of the trileaflet porcine tissue valve 36. A plurality of relatively small round holes or apertures 74 are disposed in the stent 32. The holes 74 accept stitches 50 whereby the fabric mesh of the second cloth tube 62 is sewn to enclose the stent 32. This is well illustrated in FIGS. 2, 3, 4, and 5.

A principal novel feature of the stent 32 is that it is made of a solid plate 76, rather than of bent metal wire (not shown). This is advantageous because the solid stent 32 of the present invention has no undue structural strain caused by excessive bending (as in prior art bent wire stents), and is made from significantly thinner (approximately ten times thinner) metal plate than the wire (not shown) of prior art wire stents (not shown). The plate 76 of the stent 32 of the present invention is typically and approximately 0.005 to 0.010 inch thick. Instead of the round holes 74, slots (not shown) or like equivalents of holes, may also be used in the stent 32 to accept the stitches 50. A process for fabricating the stent 32 of the present invention is described below.

Referring now again principally to FIGS. 3, 5, 9, and 10, the stent 32 is shown affixed in the cloth pocket 67 formed from the second cloth tube 62 which is itself embedded in the stent support ring 34. These figures also show the stent 32 and stent support ring 34 mounted to the sewing ring 30, as the structure is assembled after implantation in the heart (not shown). As it was noted above, the porcine tissue valve 36, which is mounted by stitches 50 to the cloth covering of the stent 32, is omitted from the drawing Figures for simplicity of illustration. A shoulder or lip 78 is incorporated into the plastic body 48 of the sewing ring 30 to set the limit how far the stent support ring 34 can be threaded into the sewing ring 30.

The manner of surgically implanting the novel heart valve prostheses of the present invention should be readily apparent from the foregoing description. Thus, the surgeon (not shown) first implants the sewing ring 30 into the mitral, aortic or tricuspid annulus (not shown). Therafter, the stent support ring 34 which bears the stent 32 and the porcine tissue valve 36, is threadably mounted into the sewing ring 30. The square threads 40 of the sewing ring 30 readily engage the like threads 58 of the stent support ring 34 within approximately one turn or less. The pressure of the stent support ring 34 on the lip 78 locks the stent support ring 34 into operative position in the sewing ring 30. If the heart valve prosthesis must be replaced at a later time, for example because of calcification of the porcine trileaflet valve 36, then removal of the stent support ring 34 from the sewing ring 30 is relatively easy because the square threads readily separate from one another. It should be readily apparent from the foregoing that the sewing ring 30 of the heart valve prosthesis of the present invention does not need to be replaced to replace a defective porcine tissue valve 36.

An inspection of the drawing Figures, principallly of FIGS. 9 and 10, reveals that there are no exposed plastic or metal surfaces in the heart valve prosthesis of the present invention. Thus, at least sometime after the implantation of the heart valve prosthesis of the present invention, the patient (not shown) may be gradually taken off anti-thrombogenic medication. This is because, as soon as the cloth enclosing the prosthesis is covered by human tissue, there are no exposed thrombogenic surfaces in the prosthesis and no further danger of embolus formation.

In alternative preferred embodiments of the heart valve prostheses of the present invention, the cloth covering the prosthesis may be coated, before implantation, with collagen fibers reconstituted from purified natural collagen and cross linked by the $NH_2$ groups to the underlying polyester fabric. Additional coatings of this "artificial" collagen layer with mucopolysacharides and/or proteins is also possible. The foregoing reduce the thrombogenecity of the implant at the time of implantation.

It should also be readily appreciated by those skilled in the art, that the thin stent 32 used in the heart valve prosthesis of the present invention results in a larger flow-through area in the mitral, aortic or tricuspid annulus (not shown), than would be possible with prior art prostheses having substantially thicker wire and/or plastic stents (not shown). For some patients, particularly for those with weak heart muscle function, the foregoing advantage may provide the ability to perform certain vigorous physical activities, which might not be possible with prostheses having the prior art wire and-/or plastic stents (not shown).

Referring now to FIGS. 11 through 14, the process of making the novel stent 32 of the present invention is disclosed. A flat plate 76 of the shape shown in FIG. 11, is formed first by laser cutting, electrode discharge machining, electron beam machining, stamping or chemical etching, with laser cutting being preferred. The plate 76 is made of stainless steel, or preferably ELGILOY, and is approximately 0.005 to 0.010 inch thick. The apertures 74, or in alternative embodiments, slots (not shown), are also preferably laser cut into plate 76.

The flat plate 76, having substantially the shape shown on FIG. 11 is thereafter bent by passing through suitable rollers (not shown) into the configuration shown in FIG. 12. The bending of the plate 76 is uniform through the whole body of the plate 76, so that no sharp bends or undue stresses arise in the plate 76. Two, preferably obliquely cut, edges 80 of the plate 76 are then brought into contact with one another, as shown on FIG. 12, and the plate 76 is secured into its final tubular configuration by resistance welding a small fastener plate 82 within its interior. This is shown on FIGS. 13 and 14.

After the step of welding, sharp edges of the intermediate stent 32 are removed by tumbling the intermediate for several hours, (preferably approximately 24 hours) with aluminum oxide (Al₂O₃) rocks, or like abrasive material. The resulting stent 32, is sewn into the cloth pocket 67 embedded in the stent support ring 32, as it was described above in detail.

Referring now to FIGS. 15 through 19, the process of making the novel sewing ring 30 and stent support ring 34 of the present invention is disclosed. The hereinbelow described process is actually suitable for making various plastic surgical implant and other items which must have a fabric securely fastened to the plastic body of the item. Therefore, in this respect the invention is broader than the fabrication of components for heart valve prosthesis. Nevertheless, the process is illustrated hereinbelow by the specific example of the preparation of the sewing ring 30 and stent support ring 34 of the heart valve prosthesis of the present invention.

Thus, a die or mold 84 specifically adapted for the making of the sewing ring 30 is shown schematically on FIG. 15. The mold 84 has suitable cavities 86 where the excess of the first cloth tube 38 is accomodated. A mandrel 88 fixedly attached to a bottom piece 90 of the mold 84 has cavities 92 which correspond to the shape of the interior threads 40 of the sewing ring 30. A plurality of ducts 94 are incorporated in the mold 84 to permit liquid plastic (not shown) to flow to the mandrel 88. A cylindrical mold piece 96 is disposed on top of the mandrel 88.

For assembly of the mold 84, the first cloth tube 38 is first placed on the mandrel 88 and the cylindrical mold piece 96. Thereafter, the mold 84 is assembled with intermediate pieces 98, 100 and 102, substantially as shown on FIG. 15. The assembled mold 84, incorporating the first cloth tube 38 is preferably preheated. Thereafter, molten thermoplastic (not shown) is injected into the mold 84 under pressure to cause the molten plastic (not shown) to flow through the ducts 94 to and through the cloth 38 into the cavities 92 formed by the mandrel 88 and the adjacent mold pieces 98 and 100. In the herein disclosed preferred embodiment of the mold 84, the intermediate pieces 98, 100 and 102 which surround the cloth tube 38, are formed from two complementary pieces held together by bolts or the like (not shown). After cooling, the mold 84 is disassembled to provide the sewing ring 30 integral with the first cloth tube 38.

Figure 18:
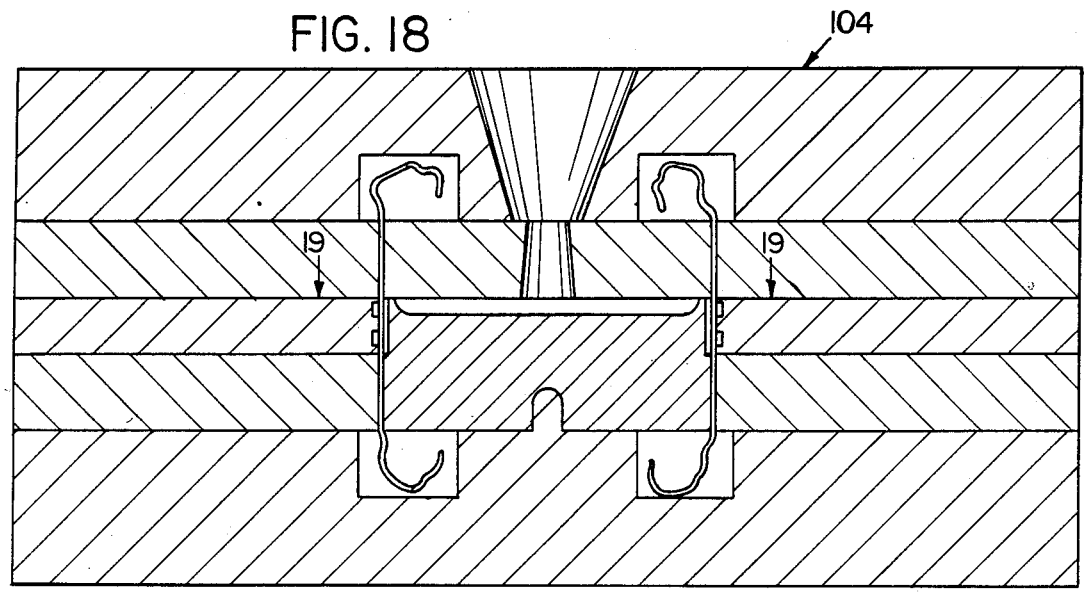
FIG. 18 is a cross-sectional view of a mold used in the process of fabricating the novel stent support ring of the present invention.
Figure 19:
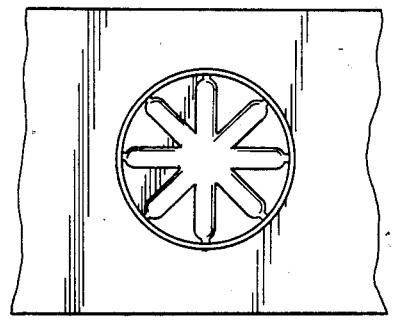
FIG. 19 is a partial plan view taken on lines 19,19 of FIG. 18.

FIGS. 18 and 19 depict a mold 104 for the making of the stent support ring 34. Description of this mold 104 is not considered necessary here, since it construction and operation can be readily understood from the description of the mold 84 which is used for making the sewing ring 30.

Those skilled in the art of plastic molding, and in the related medical technological arts will readily recognize that several modifications of the molds 84 and 104 and of the hereinbelow described specific process parameters are possible to make the novel composite fabric and plastic items of the invention. Therefore, the ensuing description of the specific parameters of the molding process should be considered examplary rather than limiting in nature.

Thus, the molds 84 and 104 are preferably made of aluminum. Biologically implantable polyester (DACRON) cloth woven in the shape of a tube is placed into the mold 84, or the mold 104. The mold is then preheated to approximately 180 Fahrenheit. The mold is used in a Morgan injection machine, wherein biologically implantable polyacetal (Dupont, DELRIN) plastic is heated to approximately 425 to 450 Fahrenheit. The melt is injected into the mold at approximately 4000 PSI pressure. After the mold is sufficiently cooled, it is disassembled to provide the composite plastic cloth sewing ring 30, or stent support ring 34.

Several modifications of the above described novel heart valve prostheses and of the associated part and processes may become readily apparent to those skilled in the art in light of the above disclosure. Therefore, the scope of the present invention should be interpreted solely from the following claims.

What is claimed is:

1. A method of fabrication of a stent for an artificial heart valve comprising:
   cutting a plate of metal having a thickness of 0.010 inches or less to produce an elongated stent member having a first end, a second end, a lower edge, and an upper edge, said upper edge provided with three commissural posts extending therefrom;
   bending said stent member to place said first end adjacent said second end of said stent member; and
   mechanically coupling said first end to said second end of said stent member.

2. A method according to claim 1 wherein said step of bending said stent member to bring said first end adjacent to said second end further comprises the step of passing said stent member through rollers to impart a uniform bend to the stent member from said first end of said stent member to said second end of said stent member.

3. A method according to claim 1 wherein said step of mechanically coupling said first end of said stent member to said second end of said stent member comprises welding.

4. A method of fabricating a stent for an artificial heart valve comprising cutting a metal plate having a thickness of about 0.005 to 0.010 inches to produce an elongated stent member having a first end, a second end, a lower edge, and an upper edge, and having three commissural posts extending from said upper edge;
   bending said stent member to place said first end of said stent member adjacent said second end of said stent member such that said stent member assumes a generally tubular configuration; and
   mechanically coupling said first end of said stent member to said second end of said stent member.

5. A method according to claim 1, 2, 3 or 4 wherein said cutting step comprises cutting said stent member from a sheet of Elgiloy.

6. A method according to claim 1, 2, 3, or 4 wherein said cutting step comprises cutting said stent member from a sheet of stainless steel.

* * * * *